(12) United States Patent
Celinska et al.

(10) Patent No.: US 6,376,691 B1
(45) Date of Patent: Apr. 23, 2002

(54) METAL ORGANIC PRECURSORS FOR TRANSPARENT METAL OXIDE THIN FILMS AND METHOD OF MAKING SAME

(75) Inventors: Jolanta Celinska; Carlos A. Paz de Araujo; Joseph D. Cuchiaro; Jeffrey W. Bacon; Larry D. McMillan, all of Colorado Springs, CO (US)

(73) Assignee: Symetrix Corporation, Colorado Springs, CO (US)

( * ) Notice: Subject to any disclaimer, the term of this patent is extended or adjusted under 35 U.S.C. 154(b) by 0 days.

(21) Appl. No.: 09/388,044

(22) Filed: Sep. 1, 1999

(51) Int. Cl.$^7$ ............................ C07F 19/00; C07F 3/00; C09K 3/00
(52) U.S. Cl. ............................ 556/28; 556/42; 556/44; 556/51; 556/54; 556/55; 556/76; 556/77; 556/78; 556/81; 556/105; 556/442; 556/482; 556/483; 556/1; 252/182.3; 534/15
(58) Field of Search ................................ 556/1, 42, 44, 556/51, 54, 55, 76, 77, 78, 81, 105, 442, 482, 483, 28; 252/182.3; 534/15

(56) References Cited

U.S. PATENT DOCUMENTS

| | | | |
|---|---|---|---|
| 3,067,356 A | | 12/1962 | Ray ............................ 313/221 |
| 3,211,768 A | * | 10/1965 | Considine .................... 260/414 |
| 3,624,444 A | | 11/1971 | Berthold et al. ............. 313/221 |
| 3,967,153 A | | 6/1976 | Milke et al. ................. 313/489 |
| 4,338,544 A | | 7/1982 | Komiya et al. .............. 313/489 |
| 4,363,998 A | | 12/1982 | Graff et al. .................. 313/487 |
| 4,507,245 A | * | 3/1985 | Ozaki et al. ............... 260/429.2 |
| 4,859,861 A | | 8/1989 | Yamanaka et al. ........... 350/336 |
| 5,071,818 A | * | 12/1991 | Kolts .......................... 502/324 |
| 5,131,065 A | | 7/1992 | Briggs et al. ................ 385/120 |
| 5,164,799 A | | 11/1992 | Yasuhiro ..................... 313/509 |
| 5,338,951 A | | 8/1994 | Argos, Jr. et al. ........... 257/295 |
| 5,384,517 A | | 1/1995 | Yasuhiro Uno ........... 315/169.3 |
| 5,539,277 A | | 7/1996 | Jansma ........................ 313/489 |
| 5,559,260 A | | 9/1996 | Scott et al. .................... 556/28 |
| 5,619,096 A | | 4/1997 | Kaliszewski et al. ........ 313/485 |
| 5,634,835 A | | 6/1997 | Wu et al. ....................... 445/24 |
| 5,721,009 A | * | 2/1998 | Dougherty et al. ....... 427/126.6 |
| 5,834,058 A | * | 11/1998 | Wallbridge et al. .......... 427/452 |

FOREIGN PATENT DOCUMENTS

| | | |
|---|---|---|
| JP | 5-28969 | 2/1993 |
| JP | 219-92211 | 4/1997 |

OTHER PUBLICATIONS

Weber et al., "Materials and Manufacturing Issues for Color Plasma Displays" MRS Bulletin, p. 65–68 (Mar., 1996).

* cited by examiner

*Primary Examiner*—Porfirio Nazario-Gonzalez
(74) *Attorney, Agent, or Firm*—Patton Boggs LLP

(57) ABSTRACT

A liquid precursor for forming a transparent metal oxide thin film comprises a first organic precursor compound. In one embodiment, the liquid precursor is for making a conductive thin film. In this embodiment, the liquid precursor contains a first metal from the group including tin, antimony, and indium dissolved in an organic solvent. The liquid precursor preferably comprises a second organic precursor compound containing a second metal from the same group. Also, the liquid precursor preferably comprises an organic dopant precursor compound containing a metal selected from the group including niobium, tantalum, bismuth, cerium, yttrium, titanium, zirconium, hafnium, silicon, aluminum, zinc and magnesium. Liquid precursors containing a plurality of metals have a longer shelf life. The addition of an organic dopant precursor compound containing a metal, such as niobium, tantalum or bismuth, to the liquid precursor enhances control of the conductivity of the resulting transparent conductor. In a second embodiment, a liquid precursor for forming a transparent metal oxide nonconductive thin film comprises an organic precursor compound containing a metal from the group including cerium, yttrium, titanium, zirconium, hafnium, silicon, aluminum, niobium, tantalum, and bismuth. Liquid precursors of the invention preferably comprise a metal organic precursor compound, such as an ethylhexanoate, an octanoate, or a neodecanoate, dissolved in a solvent, such as xylenes, n-octane and n-butyl acetate.

27 Claims, 7 Drawing Sheets

METAL ORGANIC PRECURSORS FOR TRANSPARENT METAL OXIDE THIN FILMS AND METHOD OF MAKING SAME

BACKGROUND OF THE INVENTION

1. Field of the Invention

This invention relates to metal oxides useful in making transparent electrodes and conductive layers, protective layers for such conductive layers and dielectric layers in flat panel displays, fluorescent lamps and other electrooptical devices, and more particularly to liquid precursors for making such transparent metal oxides and methods for making such precursors.

2. Statement of the Problem

A typical fluorescent lamp comprises a cylindrical glass tube or envelope containing mercury vapor and a phosphor layer covering the inside of the tube wall. Many fluorescent lamps, in particular rapid-start fluorescent lamps, usually comprise one or more transparent metal oxide layers; for example, an electrically conductive metal oxide layer on the inner surface of the glass tube, and a metal oxide protective layer between the conductive layer and the phosphor layer of the lamp.

A conventional technique of the art of forming transparent metal oxide layers in fluorescent lamps involves: dispersing a solid powder of the desired oxide in a liquid medium to make a colloidal suspension of the oxide; applying a coating of the suspension onto a surface of the lamp; and drying the coating to form the oxide layer. Generally, it is difficult to achieve a uniform, continuous thin film by applying a colloidal suspension of powdered particles. Another technique involves dissolving a precursor compound in a solvent and spraying the precursor solution onto a hot surface having a temperature above the crystallization temperature of the desired oxide, whereby the precursor compound is immediately pyrolyzed. A typical conventional precursor for a conductive layer contains tin tetrachloride, $SnCl_4$, and hydrogen fluoride, HF, in butanol. The chlorine and fluorine are highly electronegative, salt-forming atoms that may lead to lamp defects called "measles", as described below. Further, highly reactive precursor compounds such as $SnCl_4$ and HF are toxic and difficult to handle, and do not store well.

It is known in the flourescent lamp art to employ a protective layer of aluminum oxide, often called alumina, or certain other metal oxides, such as oxides of cerium, yttrium, titanium, and zirconium to inhibit or delay discoloration and other appearance defects in the phosphor layer or the conductive oxide layer. Silicon oxide, often referred to as silica, may also be included in a protective layer. These barrier layers of the prior art are located between the conductive oxide layer and the phosphor layer. The advantages of the protective coating are probably a result of the relatively nonporous metal oxide coating that protects the conductive oxide layer from ion bombardment resulting from arc discharge. The protective layer is generally formed utilizing an aqueous colloidal suspension or a dispersion of the metal oxide in a liquid. As indicated above, it is difficult to deposit a continuous solid layer using a colloidal suspension or a dispersion. Another typical conventional precursor for a protective layer is a metal alkyl compound in a solvent, which is pyrolyzed. It is generally difficult to form a uniform, continuous metal oxide thin film by the conventional pyrolysis method of the prior art because pyrolysis of the sprayed precursor compound on the hot substrate results in a broken, uneven surface on the microscopic level.

Flat panel displays typically comprise one or more layers of transparent metal oxide thin films. Transparent conductive metal oxide thin films commonly serve as electrodes between the light source and the viewing surface to assist in establishing electric fields for operating the display. It is usual for thousands of metal oxide electrodes to be formed. The electrodes must necessarily be transparent so that they do not interfere with the intensity and quality of the light images produced for display. A flat panel display often also comprises one or more transparent nonconductive metal oxide thin films that serve as insulators or protective coatings in the display. These metal oxide thin films are typically deposited using sputtering techniques that are complex and unreliable. Conventional deposition techniques often result in problems, such as poor adherence of the thin films to their substrate and "pinhole" defects in the deposited thin film.

SOLUTION

The present invention provides novel precursors for forming transparent metal oxide thin film layers in a fluorescent lamp, a flat panel display or other electrooptical device. In particular, the invention provides novel nonaqueous metal organic liquid precursor solutions ("liquid precursors") and methods of making such precursors.

In one embodiment, the invention provides a novel liquid precursor for forming a transparent, electrically conductive metal oxide thin film layer ("conductive layer"), which may be used, for example, in a fluorescent lamp.

The invention further provides a novel liquid precursor for forming an electrically nonconductive metal oxide protective layer("protective layer"), which may be used, for example, between the phosphor layer and the conductive layer of a fluorescent lamp. The inventive metal organic precursors may be used to fabricate a wide variety of metal oxide thin film layers.

The invention further provides a novel liquid precursor for forming an electrically conductive metal oxide thin film as a transparent electrode in a flat panel display.

A nonaqueous metal organic liquid precursor solution ("liquid precursor") of the invention is usually applied to a substrate surface using a liquid source deposition technique. The liquid precursor contains one or more metal organic precursor compounds that lead to formation of the desired metal oxide thin film layer upon reaction and crystallization on the substrate surface. Usually, the desired oxide is a metal oxide; therefore, the liquid precursor usually contains a metal organic precursor compound. The oxide formed by the inventive liquid precursor may also be a nonmetallic oxide, such as silicon oxide, in which case the organic precursor compound of the liquid precursor is also nonmetallic. An inventive liquid precursor is a solution of one or more organic compounds dissolved in a nonaqueous solvent. The precursor is applied to the substrate surface and treated, usually by one or more heating techniques. As a result, the organic precursor compound or compounds react to form a solid thin film having the desired composition on the substrate surface. In the fabrication of a fluorescent lamp, the lamp envelope may be dipped or rolled in liquid precursor to form a liquid coating of precursor, which is then treated; the liquid precursor solution may also be applied using a conventional liquid spraying method, as known in the fluorescent lamp art. In the fabrication of flat panel displays, fluorescent lamps and other electrooptical devices, the liquid precursor is often applied by a liquid misted deposition method, in which a very fine mist of liquid particles is formed in a carrier gas and deposited on the substrate surface.

A nonaqueous metal organic liquid precursor solution of the invention comprises an organic precursor compound containing a first metal selected from the group including tin, antimony, indium, niobium, tantalum, bismuth, cerium, yttrium, titanium, zirconium, hafnium, and silicon. In one embodiment, the first metal is selected from the group consisting of tin, antimony, indium to make a conductive metal oxide material that may include $SnO_2$, $Sb_2O_3$, and $In_2O_3$. In this embodiment, the liquid precursor preferably further comprises an organic dopant precursor compound containing a metal selected from the group including niobium, tantalum, bismuth, cerium, yttrium, titanium, zirconium, hafnium, silicon, zinc and magnesium. In another embodiment of the invention, the liquid precursor comprises an organic precursor compound containing a metal selected from the group including cerium, yttrium, titanium, zirconium, hafnium, silicon, niobium, tantalum, and bismuth. Thus, the liquid precursor contains metal moieties in effective amounts for forming one or more oxides selected from the group including $Ce_2O_3$, $Y_2O_3$, $TiO_2$, $ZrO_2$, $HfO_2$, $SiO_2$, $Nb_2O_5$, $Ta_2O_5$, and $Bi_2O_3$.

According to the invention, the liquid precursor solution discussed above is applied to the substrate surface, and then a solid metal oxide is formed in heating steps subsequent to the liquid application step. In this regard, the invention has two significant aspects: 1) the liquid precursor is a solution of a metal precursor compound, not a colloidal suspension or dispersion of the material to be deposited; and 2) the liquid precursor solution has an opportunity to distribute itself on the substrate surface before a solid is formed. These aspects of the invention may be employed alone or in combination. Both of these aspects contribute to the formation of a continuous, uniform layer of solid on the substrate surface. Since the liquid is a solution of a metal compound, the distribution of the metal elements is inherently uniform in the liquid. Since the liquid has an opportunity to distribute itself before solidifying, advantage can be taken from the natural tendency of a liquid, as compared to a solid, to distribute itself evenly.

The metal organic liquid precursor solutions of the invention are chemically stable, so they can be prepared in advance and stored safely for relatively long periods, up to six months. Initial precursors for a plurality of different constituents and dopants may be dissolved in the same final liquid precursor, so that the composition of the metal oxide thin film layer can be easily varied and controlled.

The metal organic liquid precursors of the invention do not contain chlorine or other highly electronegative salt-forming atoms. Chlorine and other salt-forming atoms contained in precursors of the prior art are starting points of measle defects in fluorescent lamps.

The inventive nonaqueous metal organic liquid precursor solutions may be used to manufacture conductive layers using a wide variety of different metal organic precursor compounds to form a wide variety of metal oxide materials, with or without dopants. An inventive liquid precursor solution may include an organic dopant precursor compound.

The preferred liquid precursor used for making a conductive layer comprises a 0.5 molar solution of tin 2-ethylhexanoate and antimony 2-ethylhexanoate in 2-ethylhexanoic acid and n-octane, containing niobium 2-ethylhexanoate, in relative molar proportions corresponding to the stoichiometric formula $Sn_{0.97}Sb_{0.03}O_2$ with 0.006 mole percent $Nb_2O_5$. In other conductive layers having good properties, the dopants may be $Ta_2O_5$ and $Bi_2O_3$. The composition of the inventive metal organic liquid precursor solutions and resulting metal oxide layers avoids the generation of measle defects during fluorescent lamp operation. The resistivity profile in a conductive layer fabricated using an inventive liquid precursor can be controlled by selection of liquid precursor composition and treating temperatures. It is understood that an inventive precursor may have a composition different from the preferred composition, and that an inventive precursor may be used to form a metal oxide thin film with a composition different from the preferred composition of thin film.

The novel precursors of the invention may be used advantageously to fabricate metal oxide protective layers in fluorescent lamps and other devices, usually comprising a single metal oxide, such as $Y_2O_3$ or $Ce_2O_3$. The inventive precursors may also be used to fabricate metal oxide thin film layers in fluorescent lamps besides a conductive layer or a protective layer. For example, the fabrication of some fluorescent lamps may include formation of an electrically nonconductive metal oxide layer on the lamp envelope surface between the envelope wall and a conductive layer.

Precursors according to the invention are also useful in the fabrication of flat panel displays. A flat panel display typically comprises one or more layers of transparent metal oxide thin films. Transparent thin films are important because they do not interfere with the display screen image when viewed from the front, or with the passage of backlighting from the back of the display. Transparent conductive metal oxide thin films commonly serve as electrodes between the light source and the viewing surface to assist in establishing electric fields for operating the display. In flat panel displays, transparent thin film layers of indium oxide, tin oxide, indium tin oxide ("ITO") or other conductive metal oxide may be formed using an inventive liquid precursor. A flat panel display often also comprises one or more transparent nonconductive metal oxide thin films that serve as dielectric insulators or protective coatings in the display. An inventive liquid precursor allows use of a liquid source deposition technique instead of conventional target sputtering or CVD techniques.

Metal organic liquid precursors according to the invention can be manufactured reliably. Their composition can be easily controlled and varied, if necessary. They can be safely stored for long periods, up to six months. They are relatively nontoxic and nonvolatile, compared to precursors of the prior art. Metal oxide thin film layers formed using liquid precursors of the invention have smooth, continuous and uniform surfaces, especially compared to oxide layers of the prior art. They can be reliably fabricated to have thicknesses in the range of 20–500 nm , maintaining important characteristics such as transparency and desired electrical properties.

The composition of a liquid precursor of the invention may be selected to provide a transparent metal oxide thin film having desired electrical properties, such as electrical conductivity, depending on a set of fabrication conditions. The electrical conductivity of a metal oxide thin film formed using an inventive precursor may vary with such factors as annealing temperature, annealing time, composition of ambient atmosphere during fabrication steps, and film thickness, among others. An important advantage of the invention is that the concentrations of a plurality of organic precursor compounds and organic precursor dopant compounds in an inventive liquid precursor may be easily and controllably varied and used in a deposition process to produce a desired metal oxide thin film for given fabrication steps.

Numerous other features, objects and advantages of the invention will become apparent from the following description when read in conjunction with the accompanying drawings.

DETAILED DESCRIPTION OF THE PREFERRED EMBODIMENT

1. Introduction

It should be understood that FIGS. 1–4, depicting fluorescent lamp and flat panel display structures, are not meant to be actual plan or cross-sectional views of any particular portion of actual electrooptical devices. In the actual devices, the layers may not be as regular and the thicknesses may have different proportions. The figures instead show idealized representations which are employed only to depict more clearly and fully the use of nonaqueous metal organic liquid precursors of the invention than would other wise be possible.

Figure 1:
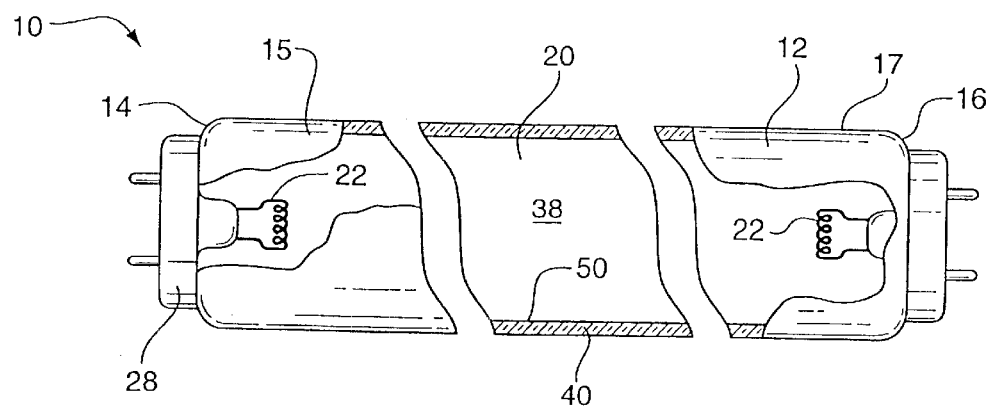
FIG. 1 shows a cross-sectional diagrammatic view of a finished fluorescent lamp fabricated in accordance with a preferred embodiment of the invention.

FIG. 1 shows a cross-sectional diagrammatic view of a finished fluorescent lamp 10 fabricated using a preferred embodiment of the inventive liquid precursor. Fluorescent lamp 10 comprises an elongated, light-transmitting envelope 12. In the embodiment depicted in FIG. 1, envelope 12 is a cylindrical glass tube. Envelope 12 typically comprises conventional soda glass, having a soda lime ($Na_2O$) content of 15% to 25%.

Figure 2:
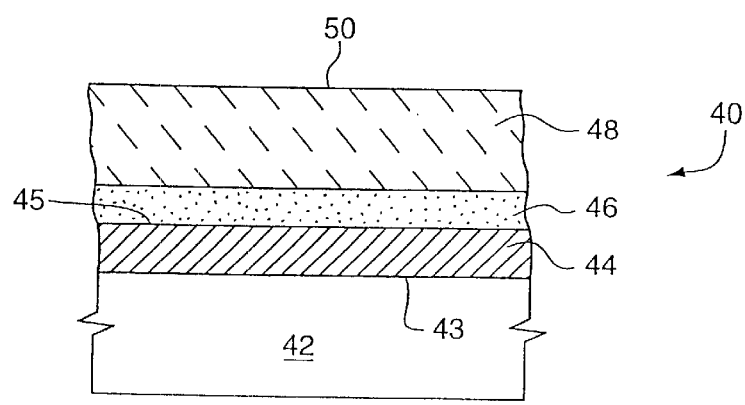
FIG. 2 shows a cross-sectional diagrammatic view of the lamp wall of the fluorescent lamp of FIG. 1.

Fluorescent lamp 10 has a lamp wall 40. As depicted in FIG. 2, lamp wall 40 comprises: an envelope wall 42 of envelope 12, having an inner envelope surface 43; a conductive layer 44; a protective layer 46; and a phosphor layer 48. In FIGS. 1 and 2, inner lamp wall surface 50 is the top surface of phosphor layer 48, contiguous with interior space 38. But in intermediate stages of fabrication not depicted herein, inner lamp wall surface contiguous to interior space 38 and on which another layer may be formed is the top surface of the uppermost layer existing in a particular stage of fabrication. For example, with reference to FIG. 2, prior to formation of any of layers 44, 46, and 48, the lamp wall is simply envelope wall 42, and the inner lamp wall surface is inner envelope surface 43; after formation of conductive layer 44, but before formation of protective layer 46, the inner lamp wall surface is surface 45 of conductive layer 44. Conductive layer 44, phosphor layer 48 and the other layers included in lamp wall 40 are circumferentially continuous and axially continuous.

In FIG. 1, lamp wall 40 has a first end 14. Associated with first end 14 is a first wall portion 15. Lamp wall 40 also has a second end 16. Associated with second end 16 is a third wall portion 17. A middle or second wall portion 20 is disposed between first wall portion 15 and third wall portion 17. Electrodes 22 are located at ends 14, 16.

Figure 7:
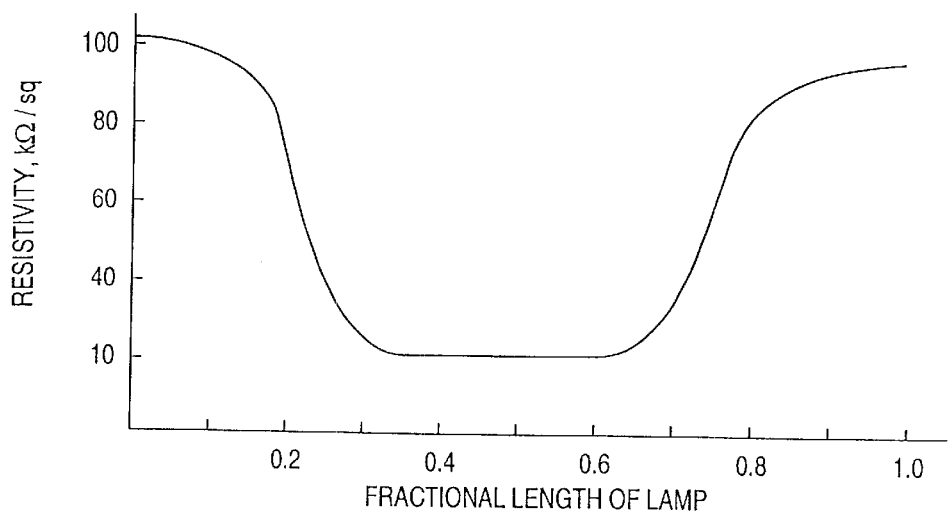
FIG. 7 is a graph of a U-shaped differential resistivity profile in the conductive layer of a fluorescent lamp fabricated using a liquid precursor of the invention.

In FIG. 2, conductive layer 44 is formed using a liquid precursor in accordance with the invention. Conductive layer 44 is a transparent, electrically conductive metal oxide thin film having the stoichiometric formula $Sn_{1-x}Sb_xO_2$, where $0.001 \leq x \leq 0.3$, combined with a dopant selected from the group including $Nb_2O_5$, $Ta_2O_5$ and $Bi_2O_3$, with a relative molar concentration in the range of 0.001 to 1.0 weight percent. Preferably, conductive layer 44 comprises metal oxide material formed using a liquid precursor containing metal amounts corresponding to the stoichiometric formula $Sn_{0.97}Sb_{0.03}O_2$ with 0.006 mole percent $Nb_2O_5$, dopant. Conductive layer 44 has a thickness in the range of 30 to 400 nm, preferably in the range of 60 to 80 nm. As explained in more detail below, the electrical resistivity of conductive layer 44 depends on the annealing temperature used during formation of conductive layer 44. The resistivity of conductive layer 44 may be uniform along the axial length of envelope 12. In a preferred embodiment, however, the resistivity varies along the axial length of envelope 12 such that the resistivity is high in end wall portions 15, 17, i.e., the first and third wall portions, and low in the middle or second portion 20. Preferably, the electrical resistivity of conductive layer 44 in first and third portions 15,17 is about 100 kΩ/square. Preferably, the electrical resistivity of conductive layer 44 in middle portion 20 is about 10 kΩ/square. It is not necessary that end portions 15, 17 and middle portion 20 have precise edges or boundaries. End portions 15,17 typically extend an axial distance equal to about from 10% to about 25% of the total axial length of envelope 12, preferably about 20%. Thus, in a fluorescent lamp having an axial length of 120 cm, end portions 15,17 preferably are each about 24 cm in length, proximate to ends 14,16. Middle portion 20, therefore, has a length in the range of about 50% to 80%, preferably about 60%, of the total axial length of envelope 12. FIG. 7 is a graph of a U-shaped resistivity profile of conductive layer 44, plotting the fractional length of the lamp versus resistivity in kiloohms per square (kΩ/sq.). As shown, the end portions, each comprising about 20% of the total length of the lamp, have an electrical resistivity of about 100 kΩ/square, and the middle portion has a resistivity of about 10 kΩ/square.

Another embodiment of the inventive metal organic liquid precursor is used for forming a protective layer 46 on conductive layer 44, as depicted in FIG. 2. Preferably, protective layer 46 comprises a metal oxide selected from the group including $Ce_2O_3$, $Y_2O_3$, $Nb_2O_5$, $Ta_2O_5$, $Bi_2O_3$, $ZrO_2$, $TiO_2$, $HfO_2$, and $SiO_2$. Protective layer 46 has a thickness in the range of 50 to 200 nm, preferably about 100 nm. However, wall 40 of a fluorescent lamp need not be fabricated to contain a protective layer.

Figure 3:
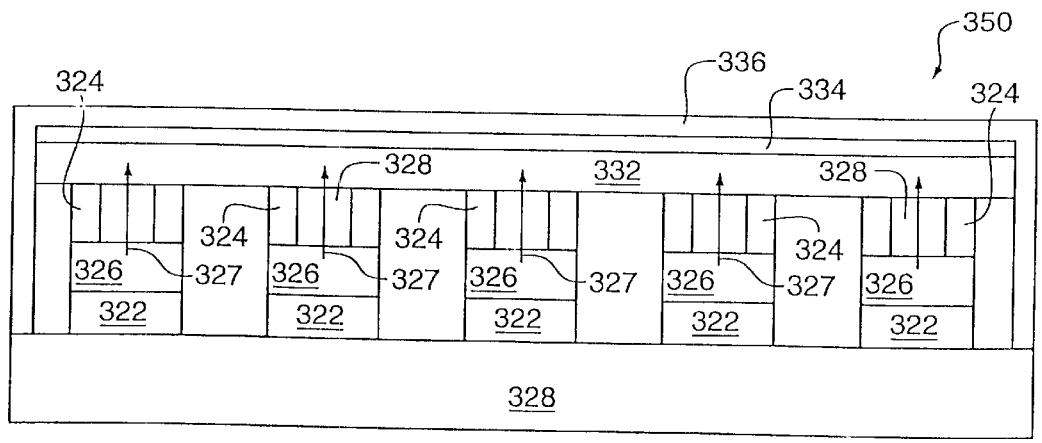
FIG. 3 is a section view of an intermediate stage in the fabrication of active-matrix electron emission luminescent display device having a transparent accelerator electrode layer.

In FIG. 3, flat panel display section 350 contains a transparent accelerator electrode 334, fabricated using a liquid precursor of the invention. Section 350 contains a plurality of display elements, or pixels, each of which includes first and second spaced apart electrodes 322 and 324, respectively, and ferroelectric thin film 326 disposed between them. First electrode 322 is preferably formed on substrate 328. Ferroelectric thin film 326 is preferably a layered superlattice material, such as strontium bismuth tantalate, $SrBi_2Ta_2O_9$, or strontium bismuth tantalum niobate, $SrBi_2Ta_{2-x}Nb_xO_9$. Preferably the ferroelectric layer is etched between adjacent electrode pairs to produce a discreet ferroelectric region for each display element. Ferroelectric thin film 326 typically has a thickness between 50 nm and 140 nm. Electrons are emitted from ferroelectric thin film 326 in an electron emission path 327 upon application of polarization switching voltages of about 10 volts or less between electrodes 322 and 324. A luminescent layer 332, such as a phosphor, is placed in electron emission path 327 so that the emitted electrons impinge thereon and cause an optical effect, namely light emission by phosphor layer 332. Substrate 328 can be any thin film or bulk material (such as MgO or $SrTiO_3$) or other material on which an appropriate template layer is deposited to yield suitable lattice matching and serve as a diffusion barrier to avoid possible destructive interactions between the substrate and the metal oxides in ferroelectric thin film 326. Semiconductors (e.g., Si, GaAs) are possible substrate materials of the latter type. Electrode layers 322, 324 each may comprise a thin film of platinum (or other metal) or a multicomponent oxide material (YBaCuO, LaSrCoO, $RuO_2$ or other conducting oxide) with a structure similar to that of the ferroelectric material. As shown in FIG. 3, first single pixel electrode 322 is preferably a solid electrode. The second single pixel electrode 324 is preferably a patterned electrode. In all cases, the patterned second electrode 324 is used to support a voltage across the ferroelectric layered superlattice material while allowing electron emission from those areas which are not covered by the electrode material. Since the emission area is increased by the patterning, more electrons are emitted, thereby producing a brighter display.

Transparent accelerator electrode layer 334 comprises a transparent conductive material, such as indium tin oxide (ITO) or antimony tin oxide. Located at the front, viewing surface 336 of the flat panel display, accelerator electrode 334 is generally maintained at a reference potential with respect to read and write voltages applied to an active matrix. Third transparent accelerator electrode layer 334 is formed using a liquid precursor according to the invention so that it is located between phosphor layer 332 and viewing surface 336. The matrix may contain a single type (i.e., wavelength emission spectrum) of phosphor or a plurality of phosphor types for providing a multicolor display. Third electrode 334 serves to accelerate electrons that are emitted from ferroelectric thin film 326 into phosphor layer 332. Typically, there is a gap 338 between phosphor layer 332 and ferroelectric layer 326. In other embodiments, gap 338 is not present, and phosphor layer 332 is formed directly on ferroelectric thin film 326.

Figure 4:
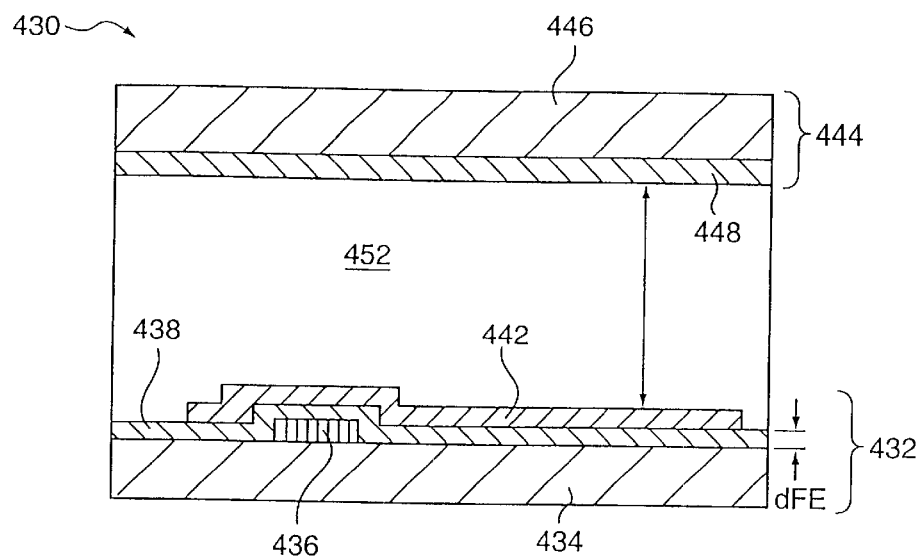
FIG. 4 is a cross-sectional illustration of a pixel portion of a liquid crystal flat panel display having transparent electrodes according to the invention.

In FIG. 4, still another embodiment of a flat panel display fabricated with an inventive precursor is shown in schematic form. FIG. 4 shows a sectional view of a one-pixel portion 430 of an active matrix type LCD (liquid crystal display) using ferroelectric material as an active portion of the driving device. The bottom substrate 432 is constituted as follows. An image electrode 436, which receives image information, is formed on a portion of glass substrate 434. Since most LCDs utilize backlighting, the image electrode comprises a transparent conductor, such as indium tin oxide (ITO) or antimony tin oxide or other transparent metal oxide thin film fabricated using an inventive liquid precursor. A ferroelectric thin film 438, preferably comprising layered superlattice material, is formed over image electrode 436 and glass substrate 434. Further, a transparent pixel electrode 442, comprising transparent metal oxide formed with a liquid precursor of the invention, is deposited over portions of image electrode 436 and ferroelectric thin film 438. A top substrate 444 comprises a glass substrate 446 and transparent scanning electrode 448, made from an inventive liquid precursor. A liquid crystal layer 452 is interposed between bottom substrate 432 and top substrate 444 to constitute a single pixel portion of a liquid crystal display.

2. Liquid Precursor Composition and Preparation

The term "thin film" as used herein generally means a film of less than a micron in thickness. The thin films disclosed herein are in all instances less than 1.0 micron in thickness. Typically, the metal oxide thin film layers of the invention have a thickness in the range of from 20 nm to 500 nm, preferably in the range of 50 nm to 200 nm. Thin films formed in accordance with the invention should not be confused with layered structures formed by wholly different processes in which the layers typically have thicknesses exceeding 1.0 micron.

The word "precursor" used herein with reference to the invention can mean a solution containing one metal organic solute that is mixed with other "precursors" to form intermediate precursors or final precursors, or it may refer to a final liquid precursor solution; that is, the solution to be applied to a particular surface during fabrication. In this disclosure, the first type of precursor is usually referred to as an "initial precursor" or designated specifically; for example, a "tin oxide precursor". The precursor as applied to the substrate is usually referred to as the "final liquid precursor", "precursor mixture", or simply "liquid precursor". In any case, the meaning is clear from the context. The composition of a precursor may be described in three ways. The actual dissolved metal organic precursor compounds (solutes) and solvents and concentrations may be specified; the relative molar proportions of chemical elements in solution may be specified; or the stoichiometric formula representing the composition of the final metal oxide material to be formed with the precursor may be specified.

The word "solution" is used in this disclosure in its technical sense, in which it means a mixture of two or more substances uniformly dispersed at the molecular level. It does not include suspensions of any type, including dispersions, colloidal suspensions or emulsions. Thus, the phrase "precursor solution" as used in this disclosure means a solution in which a compound containing an element of the final desired solid material is dissolved in a liquid solvent.

The term "stoichiometric" herein may be applied to both a solid layer of a material or to the liquid precursor for forming a material. When it is applied to a solid layer, it refers to a formula which shows the actual relative amounts of each metal element in a final solid layer. When applied to a liquid precursor, it usually indicates the molar proportion of metals in the precursor. In accordance with the invention, a metal oxide thin film deposited using an inventive liquid precursor may comprise a single one-metal oxide compound, or a single multi-metal oxide compound, or a plurality of types of oxide compounds. For example, the stoichiometric formula $Sn_{1-x}Sb_xO_2$ represents a metal oxide material in which both tin oxide and antimony oxide crystals are present. Furthermore, the subscript of oxygen used in a stoichiometric formula in this specification is commonly an approximation of the subscript value that would correspond with actual valence values of the metals in the formula and of dopants. An important feature of the invention is the presence of a dopant in a conductive metal oxide thin film layer and in the final liquid precursor solution used to form it. The term "dopant" is used here as it is commonly used in the chemical arts to refer to a relatively small amount of substance that usually does not determine the overall physico-chemical structure of the material that contains it, although it may strongly influence the material's physical properties and behavior. In this specification, a substance is considered to be a dopant if its relative concentration in the precursor or solid layer constitutes not more than 1% of the total molar concentration of the major constituents. For example, in a liquid precursor containing metal amounts corresponding to the stoichiometric formula $Sn_{0.97}Sb_{0.03}O_2$ with 0.006 mole percent $Nb_2O_5$, Sn and Sb are major constituents and Nb is a dopant. The general term "organic precursor compound" includes "organic dopant precursor compound".

Terms of orientation herein, such as "above", "top", "upper", "below", "bottom" and "lower" are relative terms, explained here by reference to FIGS. 2 and 3. In FIG. 2, the terms are interpreted relative to envelope wall 42. That is, if a second element is "above" a first element, it means the second element is farther from envelope wall 42; and if it is "below" another element, then it is closer to envelope wall 42 than the other element. The long dimension of a fluorescent lamp defines the axial and horizontal direction. Not all fluorescent lamps are straight tubes. Flourescent lamps embodying circular tubes are common. Generally, the axial and horizontal direction is the direction of the path between the two active electrodes of a lamp. The "ends" of a lamp are the portions of-the lamp envelope proximate to the electrodes, as depicted in FIG. 3. In FIG. 3, the terms of orientation are relative to substrate 328. The flat dimension of substrate 328 in FIG. 3 is considered to be the horizontal direction. If an element is "above" another element, then it is farther from substrate 328. For example, ferroelectric thin film 326 is above electrode 322. Terms such as "above" and "below" do not, by themselves, signify direct contact. But terms such as "on" or "onto" usually do signify direct contact of a layer with a contiguous layer. The term "directly on" and similar terms always signify direct contact.

The term "substrate" is sometimes used ambiguously. It can refer to the original starting material on which layers and device elements are formed, such as envelope wall 42 of FIG. 2 or substrate 328 in FIG. 6. It may also have the general meaning of any object or surface on which a material layer is directly deposited. For example, in FIG. 2, conductive layer 44 is the substrate on which protective layer 46 is deposited. In this disclosure, "substrate surface" shall generally mean the surface on which a liquid precursor is applied or a layer of material is deposited.

Terms such as "heating", "distilling", "drying", "baking", "rapid thermal process" ("RTP"), "annealing", and others all involve the application of heat. For the sake of clarity, the various terms are used to distinguish certain techniques and method steps from one another. Nevertheless, it is clear that similar techniques may be used to accomplish differently named process steps; for example, drying, baking and annealing may typically be accomplished using the same apparatus, the only differences being their function and position in a fabrication sequence, or the particular temperatures used. As a result, it would be possible to designate an annealing step as a heating step, or a drying step as a baking step. To avoid confusion, therefore, the general term "heating" may also be used to describe a fabrication step, especially in the claims describing the invention. It is further understood that one skilled in the art may accomplish a desired process result using heat as disclosed herein, while referring to the process with a term different from the one used herein.

The electrical resistivity of a conductive layer in a fluorescent lamp, as described herein, is typically in the range of from 0.5 to 300 k$\Omega$/square. The term "nonconductive" as used herein to describe a material in a fluorescent lamp signifies that the material being described has an electrical resistivity at least 100 times greater than the highest resistivity of the lamp's conductive layer. Similarly, it should be understood that the general method and precursors of the invention may be used to fabricate metal oxide thin film layers having varying degrees of resistivity in fluorescent lamps. The invention may also be used to fabricate metal oxide thin film layers in fluorescent lamps in which no conductive layer is present, or in which resistivity is not a functionally important characteristic.

Silicon oxides are often referred to in the art as metal oxides. Therefore, the terms "metal organic precursor compound" and "metal oxide" as used herein include silicon oxides and silicon-containing precursor compounds of silicon oxides.

The final precursor applied to a substrate surface may be a solution of initial precursors. Preferably, each initial precursor contains an organic precursor compound, or organic dopant precursor compound, for forming a metal oxide. An initial precursor is typically formed by mixing the metal or metals, for example, tin, or an alkoxide of the metal, with a carboxylic acid, or with a carboxylic acid and an alcohol, and conducting chemical reactions in a solvent. Metal alkoxides may be selected from a group including methoxides, ethoxides, isopropoxides, n-butoxides and pentoxides. Carboxylic acids that may be used include 2-ethylhexanoic acid, octanoic acid, and neodecanoic acid, preferably 2-ethylhexanoic acid. Alcohols that maybe used include 2-methoxyethanol, 1-butanol, 1-pentanol,2-pentanol, 1-hexanol, 2-hexanol, 3-hexanol, 2-ethyl-1-butanol, 2-ethoxyethanol, and 2-methyl-1-pentanol, preferably 2-methoxyethanol. Solvents that may be used include xylenes, n-octane, 2-methoxyethanol, n-butyl acetate, n-dimethylformamide, 2-methoxyethyl acetate, methyl isobutyl ketone, methyl isoamyl ketone, isoamyl alcohol, cyclohexanone, 2-ethoxyethanol, 2-methoxyethyl ether, methyl butyl ketone, hexyl alcohol, 2-pentanol, ethyl butyrate, nitroethane, pyrimidine, 1, 3, 5-trioxane, isobutyl isobutyrate, isobutyl propionate, propyl propionate, ethyl lactate, n-butanol, n-pentanol, 3-pentanol, toluene, ethylbenzene, 1-butanol, 1-pentanol, 2-pentanol, 1-hexanol, 2-hexanol, 3-hexanol, 2-ethyl-1-butanol, 2-ethoxyethanol, and 2-methyl-1-pentanol, as well as many others. The metal, metal alkoxide, acid, and alcohol react to form a mixture of metal-alkoxocarboxylate, metal-carboxylate and/or metal-alkoxide, which mixture is heated and stirred as necessary to form metal-oxygen-metal bonds and boil off any low-boiling point organics that are produced by the reaction. The alcohol is preferably 2-methoxyethanol or 2-methoxypropanol. The carboxylic acid is preferably 2-ethylhexanoic acid. The reaction is preferably conducted in a xylenes or n-octane solvent. The reaction of the mixture is usually conducted in a nitrogen atmosphere. The reaction may be conducted at room temperature by stirring the mixture for a time period of from 6 to 48 hours. It is often preferable to heat the mixture at a temperature in the range of from 30° C. to 200° C. to enhance the reaction. The reaction is typically conducted using a reflux condenser. To remove water and volatile organics after reaction, the reaction mixture is heated using a distillation column at a temperature from 50° C. to 200° C. Liquid precursors of the invention are typically made in batches prior to their use. It is a feature of the invention that the liquid precursors have a long shelf life and can, therefore, be stored for several months. Immediately before application of a liquid precursor to a substrate surface, final preparation steps may be conducted, including mixing, solvent exchange, and dilution. A liquid precursor is typically diluted to a concentration of from 0.1 to 0.5 moles of the desired metal organic precursor compound per liter of solution.

The solution is mixed to substantial homogeneity, and is preferably stored under an inert atmosphere of desiccated nitrogen or argon if the final solution will not be consumed within several days or weeks. This precaution in storage serves to assure that the solutions are kept essentially water-free and avoids the deleterious effects of water-induced polymerization, viscous gelling, and precipitation of metallic moieties that water can induce in alkoxide ligands. Even so, the desiccated inert storage precaution is not strictly necessary when the precursor, as is preferred, primarily consists of metals bonded to carboxylate ligands and alkoxycarboxylates. Refrigeration of an inventive precursor may extend its shelf life. The presence of a plurality of metal organic precursor compounds in the same liquid precursor solution also extends shelf life.

The precursor mixing, distillation, solvent control, and concentration control steps can be combined and/or ordered differently depending on the particular liquids used, whether one intends to store the precursor or use it immediately, and other considerations. For example, distillation is useful for removing unwanted by-products, as well as usually being part of solvent concentration control, and thus both functions are often done together. As another example, mixing and solvent control often share the same physical operation, such as adding particular reagents and solvents to the precursor solution in a predetermined order. Any of these steps of mixing, distilling, and solvent and concentration control may be repeated several times during the total process of preparing a liquid precursor.

The present invention provides novel liquid precursor solutions to make transparent metal oxide thin films. The inventive liquid precursor solutions permit the formation of transparent metal oxide thin films through a low-temperature anneal process. The low-temperature anneal enables the widespread use of these materials in flat panel displays and other electrooptical devices in which the other materials and the electronics of the device preclude high-temperature fabrication steps.

The special liquid precursors are prepared to be stable so that they have a relatively long shelf-life, at least between two and six months duration. In contrast, the solutions used in the sol-gel methods disclosed in the prior art are chemically unstable and have virtually no shelf-life. The stability of the precursors contributes to cost-efficiency and uniformity among production runs.

For liquid deposition methods, such as misted deposition and spin-on techniques, the preferred inventive liquid precursor for depositing a metal oxide thin film is a nonaqueous metal organic liquid precursor solution in which a solvent comprises xylenes, n-octane or n-butyl acetate, and a metal organic precursor compound is a metal ethylhexanoate. When a liquid precursor is prepared and stored for longer than one day, the solvent preferably comprises xylenes only and the liquid precursor has a concentration of approximately 0.5 molar. When the solution is about to be used, preferably it is diluted with n-octane or n-butyl acetate to about 0.2 molar concentration before application to a substrate. Preferred liquid precursors for oxides of tin, antimony, indium, niobium, tantalum, bismuth, cerium, yttrium, titanium, zirconium, hafnium, silicon, zinc, and magnesium, among others, comprise ethylhexanoates of these metals.

Figure 5:
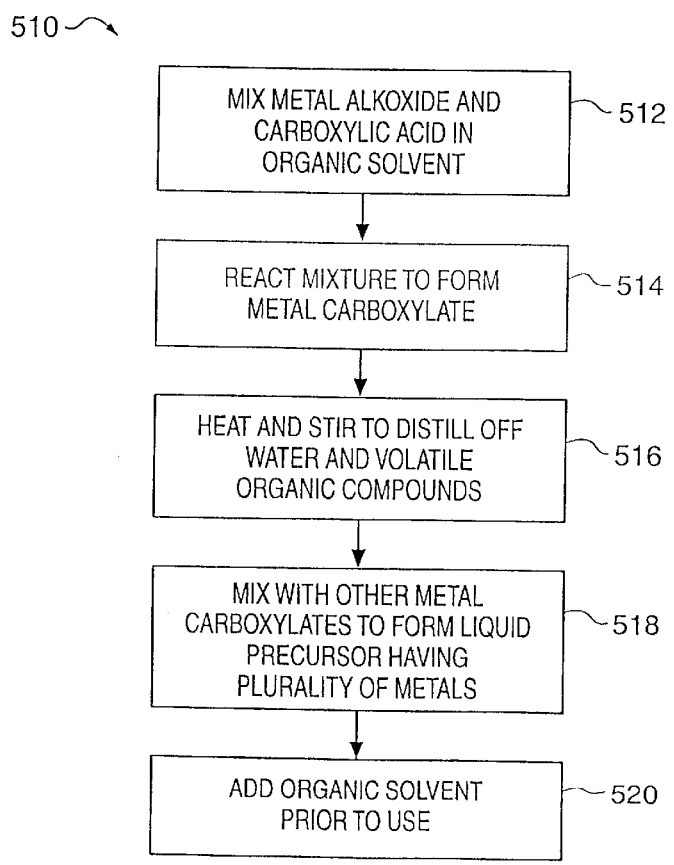
FIG. 5 depicts a flow chart of the preferred generalized method for forming a liquid precursor according to the invention.

FIG. 5 depicts a flow chart of the preferred generalized method for forming a liquid precursor according to the invention. In step 512, a first metal alkoxide is mixed with a carboxylic acid in an organic solvent. Preferably, the carboxylic acid is 2-ethylhexanoic acid, and the organic solvent is xylenes. Alternatively, a first metal may be mixed with an alcohol and a carboxylic acid in an organic solvent. In step 514, the mixture is reacted to form a metal alkoxycarboxylate, preferably a metal 2-ethylhexanoate. Reaction is accomplished by stirring for 24 hours in a nitrogen atmosphere, or by heating with reflux at about 100° C. in a nitrogen atmosphere for about 24 hours, as described in the examples below. In step 516, the solution containing the metal alkoxycarboxylate is distilled at about 70° C. to 80° C. until the head temperature falls to below 50° C., and then the solution is cooled in a nitrogen atmosphere. Step 516 serves to boil off any water and any volatile organic compounds that are produced by the reaction. Preferably, at least 50% of the metal-to-oxygen bonds of the final metal oxide desired in the thin film are formed by the end of this step. When a desired metal carboxylate, or other metal organic precursor compound, of suitable quality is commercially available, then the metal carboxylate or other type of precursor compound may be purchased instead of forming it as outlined in steps 512–516. In step 518, a plurality of metal carboxylate solutions may be mixed to produce a final precursor having the desired composition of constituent metals. A solvent exchange step may take place simultaneously or subsequently for purposes of changing the solvent portion of the precursor mixture. In step 520, usually immediately prior to use, organic solvent is added to the final precursor to adjust it to the desired concentration for deposition, usually about 0.2 molar.

Figure 6:
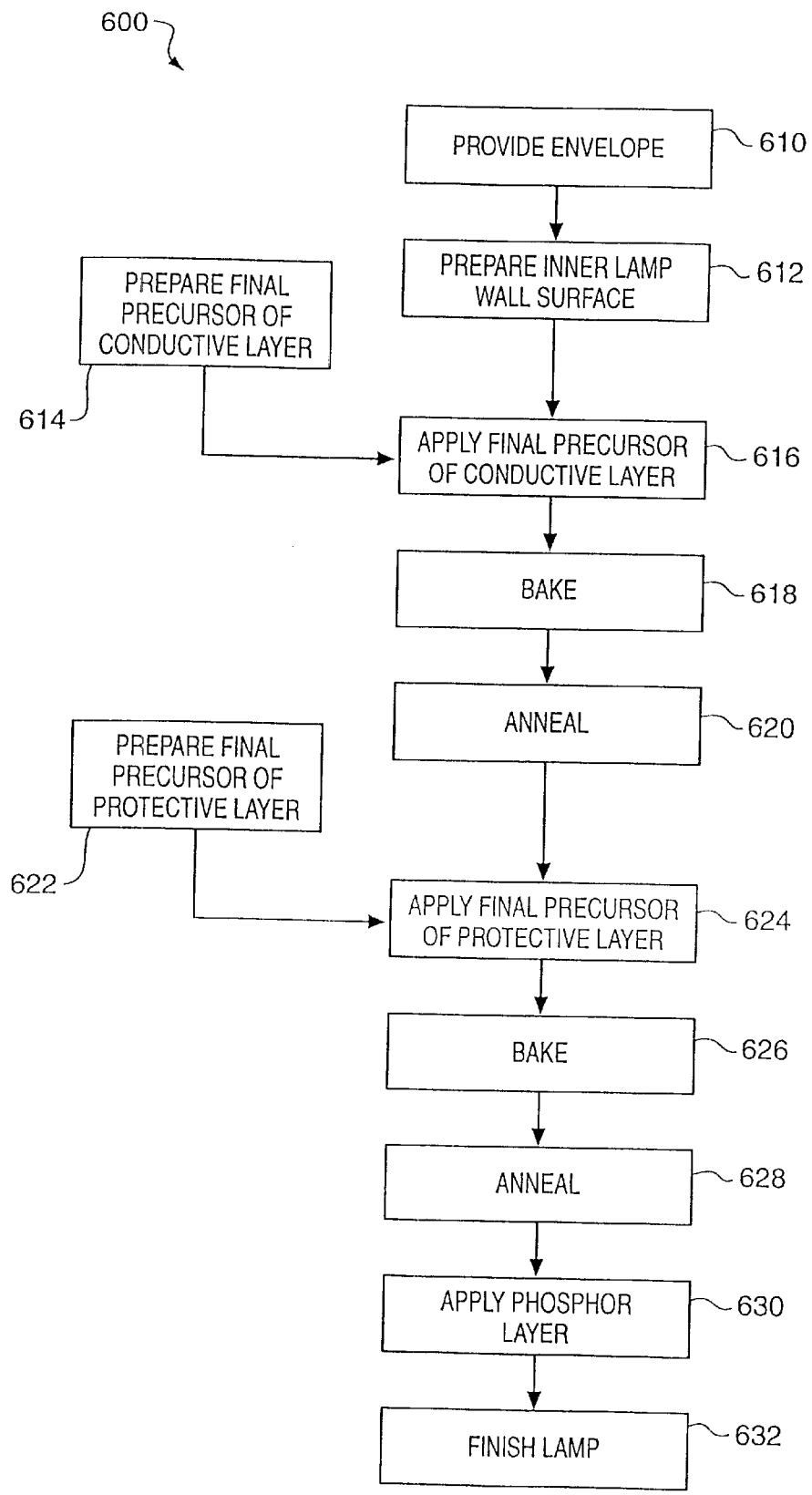
FIG. 6 is a flow chart showing the steps of a generalized liquid source deposition process for fabricating a fluorescent lamp using liquid precursors of the invention.

FIG. 6 is a flow chart showing the steps of a generalized liquid source deposition process 600 for fabricating a fluorescent lamp in accordance with an embodiment of the invention. The fabrication methods, precursors and compositions disclosed herein are discussed in relation to the structure of fluorescent lamp 10, depicted in FIGS. 1 and 2. It is understood, however, that the useful features of the invention can be applied in many variations of the generalized fabrication methods disclosed herein.

In step 610, a conventional fluorescent lamp envelope 12 is provided and in step 612 its inner envelope surface 43 is prepared using conventional techniques of the art. In step 614, a final precursor for forming conductive layer 44 is prepared.

In step 616, the final liquid precursor for the conductive layer is applied to glass inner surface 43 using any deposition process suitable for nonaqueous metal organic liquid precursors. Preferably, a conventional liquid-source spraying method of the fluorescent lamp art is used, except that the liquid is an inventive liquid precursor solution rather than a colloidal suspension of the prior art. A liquid-source misted deposition process may also be used. In a misted deposition process, a mist comprising fine liquid particles suspended in a carrier gas is flowed through the interior space of the lamp envelope, where the liquid particles deposit on inner envelope surface 43. A misted deposition process has several advantages over a spraying process, including: better control over layer thickness and uniformity; less wasted precursor; continuous operation. Or liquid precursor may be applied by rolling the envelope with liquid precursor in its interior space. In Example 3, described in detail below, a spin-on technique was used to spin the precursor solution on glass wafers. A "cold envelope" or a "hot envelope" applying technique may be used. Preferably, a cold envelope method, sometimes called a cold-tube method, is used. In a typical cold envelope technique, the inner lamp wall surface is not heated, rather it is approximately at room temperature when liquid precursor is applied to it. After application of liquid precursor to form a liquid coating, the envelope is baked, and then annealed. In a typical hot envelope technique, the envelope is heated so that the temperature of the inner lamp wall surface has a value not exceeding 300° C. when the liquid precursor is applied. After application of the precursor, a baking step is not necessary, and the envelope is annealed.

After the liquid precursor is applied in step 616, the lamp envelope is treated to form conductive layer 44. Treating may comprise a process selected from the group including: exposing to vacuum, drying, heating, baking, rapid thermal processing, and annealing. In the preferred method, treatment includes baking and annealing. In step 618, baking serves to remove the organic solvent from wall 40 and causes the metal organic precursor compounds of the precursor to decompose and react. Baking is typically performed for one minute at 160° C., then at 260° C. for four minutes.

As explained above, in a variation of process 400, the final liquid precursor may be sprayed onto or other wise applied to the inner lamp wall surface in a lamp envelope that has been heated to a temperature not exceeding 300° C. Upon application, the solvent immediately volatilizes and the organic precursor compound or compounds react, and a baking step 618 is not necessary. The lamp envelope can then be annealed. In another variation of process 400, a liquid-source chemical vapor deposition ("LSCVD") method may be used to apply the liquid precursor by vaporizing either a single final precursor or several liquid precursor solutions in a carrier gas and flowing the vaporized precursor along the heated inner lamp wall surface, where the organic precursor compounds react to form a solid thin film layer, which is then annealed. Here, "vapor" refers to a gasified precursor.

Figure 8:
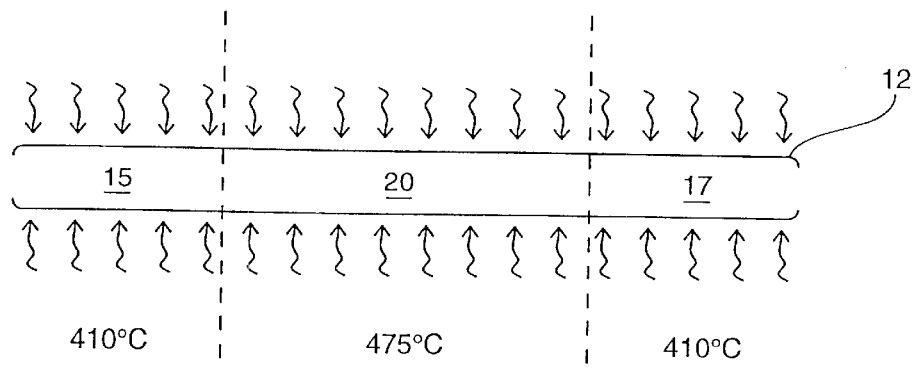
FIG. 8 is a diagrammatic view of a differential distribution of temperatures during the annealing of a conductive thin film formed with a liquid precursor of the invention.

In step 620, a furnace anneal, preferably in a reducing forming-gas atmosphere, results in crystallization or recrystallization of the desired metal oxide compounds in conductive layer 44. The forming gas atmosphere typically contains 5 to 20 volume percent $H_2$ gas mixed with nitrogen gas. Preferably, the forming gas has a composition of 10% $H_2$ gas and 90% nitrogen. The annealing is conducted at a temperature in the range of from 400° C. to 500° C. The temperature of annealing affects the resistivity of conductive layer 44. The preferred resistivity profile of conductive layer 44 is a U-shaped profile as in FIG. 7, in which the resistivity in the end portions 15,17 of wall 40 is about 100 kΩ/square, and the resistivity in middle portion 20 is about 10 kΩ/square. To achieve these approximate values, the partially completed lamp 40 is annealed in a zoned furnace, in which the temperature can be controlled to be different from one zone to the next. When conductive layer 44 comprises material having the preferred composition described above, that is, $Sn_{0.097}Sb_{0.03}O_2$, with 0.006 mole percent $Nb_2O_5$ dopant, then the desired U-shaped profile is achieved by annealing end portions 15, 17 of lamp wall 40 at 410° C., and middle portion 20 at 475° C. Such a distribution of temperatures during the annealing process is depicted in FIG. 8.

After envelope 12 including conductive layer 44 has been annealed in step 618, the phosphor layer can be applied on conductive layer 64. Nevertheless, the preferred embodiment of the invention includes forming protective layer 46 of FIG. 2. In step 622, a final precursor for protective layer 46 is prepared. A final precursor for protective layer 46 is prepared using reactants, solvents and techniques similar to those used in step 614 for preparing the final precursor of conductive layer 44. Nevertheless, a final precursor for protective layer 46 usually comprises only a single metal organic precursor compound, such as a metal carboxylate, in which the metal is one selected from the group including cerium, yttrium, niobium, tantalum, bismuth, zirconium, titanium, hafnium, silicon and aluminum. Typical metal carboxylates are ethylhexanoates, octanoates, and neodecanoates. Preferably, the final precursor prepared in step 622 comprises a 0.20 molar solution of cerium 2-ethylhexanoate in 2-ethylhexanoic acid and n-octane, as described in Example 1, below, for forming $Ce_2O_3$. Another example of a final precursor for protective layer 46 is yttrium 2-ethylhexanoate in 2-ethylhexanoic acid and n-octane for forming $Y_2O_3$.

In step 624, the final liquid precursor for protective layer 46 is applied onto conductive layer 44 using any deposition process suitable for nonaqueous metal organic liquid precursors. Preferably, a cold-envelope technique is used.

After the liquid precursor is applied in step 624, the lamp envelope is treated to form protective layer 46. Treating may comprise a process selected from the group including: exposing to vacuum, drying, heating, baking, rapid thermal processing, and annealing. In the preferred cold-envelope method, treatment includes baking and annealing. In step 626 of the preferred method, baking serves to remove the organic solvent from wall 40 and causes the metal organic precursor compounds of the precursor to decompose and react. Baking is typically performed for one minute at 160° C., then at 260° C. for four minutes. In step 628, a furnace anneal, preferably in a reducing atmosphere, results in formation and crystallization of the desired electrically nonconductive oxide material in protective layer 46. The forming gas atmosphere typically contains 5 to 20 volume percent $H_2$ gas mixed with nitrogen gas. Preferably, the forming gas has a composition of 10% $H_2$ gas and 90% nitrogen. The annealing is conducted at a temperature in the range of from 400° C. to 500° C.

In step 630, phosphor layer 48 is formed on inner lamp wall surface 50. Phosphor layer 48 is formed using conventional techniques of the art. In step 632, the fluorescent lamp is finished using conventional techniques. Step 632 typically includes inserting electrodes, injecting fill gas, sealing the envelope and mounting end caps.

EXAMPLE 1

A final liquid precursor for a conductive layer was prepared comprising a 0.5 molar solution in n-octane of tin 2-ethylhexanoate and antimony 2-ethylhexanoate in relative molar proportions corresponding to the stoichiometric formula $Sn_{0.097}Sb_{0.03}O_2$, with 0.006% (mole percent) $Nb_2O_5$ dopant.

A solution of tin 2-ethylhexanoate in 2-ethylhexanoic acid comprising approximately 28 weight percent tin was obtained from Strem Chemicals, Inc. The commercial tin-containing solution was mixed with anhydrous n-octane from Aldrich Company to adjust the concentration to 0.50 molar, filtered through a 0.2 micron filter and bottled.

Antimony n-butoxide was converted to antimony 2-ethylhexanoate. Antimony n-butoxide was obtained from Strem Chemicals, Inc. A 100 ml round-bottom flask was purged with nitrogen. Nine grams of antimony n-butoxide was combined with 3.15 equivalents of 2-ethylhexanoic acid from Aldrich Company and 15 ml anhydrous n-octane in the round-bottom flask, which was purged with nitrogen again and closed with a septum stopper. The contents of the flask were stirred with a magnetic stirrer for 24 hours. The solution in the flask was poured into a graduated cylinder and n-octane was added to adjust the concentration to exactly 0.05 molar. The solution was filtered through a 0.2 micron filter and bottled.

Niobium ethoxide was obtained from Strem Chemicals, Inc. A 100 ml round-bottom flask was purged with nitrogen. Six grams of niobium ethoxide was combined with 5.25 equivalents of 2-ethylhexanoic acid and 10 ml xylene from Aldrich Company in the round-bottom flask, which was purged with nitrogen again and connected to a reflux condenser. A slow flow of nitrogen was established into and out of the top of the condenser, and the flask was heated at 100 °C. in an oil bath while the contents of the flask were stirred with a magnetic stirrer. After 18 hours, the reflux condenser was removed, a distillation head and a condenser were attached, and the temperature of the oil bath was raised to 120° C. Distillation was conducted to reach a maximum head temperature of 72° C.; distillation was continued until the head temperature decreased to below 50° C. The flask was removed from the heat, the distillation apparatus was disassembled, and the flask was purged again with nitrogen gas while the solution was still hot. The solution in the flask was allowed to cool to room temperature. The cooled solution was poured into a graduated cylinder and xylene was added to adjust the concentration to exactly 0.05 molar (approximately 38 ml). The 0.5 molar solution was filtered through a 0.2 micron filter and bottled. Prior to making the final precursor, 0.1 ml of the niobium 2-ethylhexanoate solution was mixed with 4.9 ml of xylene to make a solution with 0.01 molar concentration.

19.4 ml of the 0.05 molar tin 2-ethylhexanoate solution was mixed with 0.6 ml of the 0.05 molar antimony 2-ethylhexanoate solution to form 20 ml of 0.05 molar liquid precursor containing tin and antimony corresponding to the stoichiometric formula $Sn_{0.97}Sb_{0.03}O_2$. 10 ml of the 0.05 molar tin-antimony solution was mixed with 0.03 ml of the 0.01 molar niobium 2-ethylhexanoate solution to form a final liquid precursor containing metal organic precursor compounds in relative molar proportions corresponding to the stoichiometric formula $Sn_{0.97}Sb_{0.03}O_2$ with 0.006 mole percent $Nb_2O_5$ dopant.

The amounts of reactants and solvents used in Example 1 may be scaled up for commercial fabrication. For reasons related to safety and handling, it is preferable to use n-octane solvent instead of xylenes in commercial-scale processes.

EXAMPLE 2

A preferred final liquid precursor for a protective layer is a 0.20 molar solution of cerium 2-ethylhexanoate in 2-ethylhexanoic acid and n-octane. A solution of cerium 2-ethylhexanoate dissolved in 2-ethylhexanoic acid (approximately 12 wt% Ce) was obtained from Aldrich Company. 23 grams of the cerium 2-ethylhexanoate solution was weighed in a 100 ml graduated cylinder, and anhydrous n-octane, also from Aldrich Company, was added to adjust the concentration to exactly 0.20 molar concentration. A stirring bar was added and the mixture was stirred until homogeneous. The solution was filtered through a 0.2 micron filter and bottled.

EXAMPLE 3

Thin films of tin-antimony oxide doped with niobium were formed on a series of silicon dioxide wafers using an inventive nonaqueous metal organic liquid precursor solution containing metal organic precursor compounds in relative molar proportions corresponding to the stoichiometric formula $Sn_{0.97}Sb_{0.03}O_2$ with 0.006 mole percent $Nb_2O_5$, in accordance with the invention. The resistivity of the thin films was measured.

To make each exemplary conductive layer, a spin-on technique was used. A final precursor was prepared as in Example 1. A few drops of the final precursor were placed on a wafer, which was spun at 3000 rpm for 30 seconds. The wafer was soft baked at 150° C. for two minutes, and hard baked at 260° C. for four minutes. The conductive layer thin film was grown by annealing the wafer at a selected temperature in the range of from 400° C. to 500° C. in forming gas with a composition of 10% $H_2$ gas in nitrogen. The thickness of the exemplary conductive layer thin films was in the range of from 60 to 80 nm. The sheet resistance of the examples was determined with a four-point probe using tungsten contacts. The resistivity of examples annealed at 410° C. was approximately 100 k$\Omega$/square. The resistivity of examples annealed at 475° C. was approximately 10 k.$\Omega$/square.

EXAMPLE 4

The shelf life of inventive liquid precursor solutions was studied. Liquid precursors were prepared, then conductive metal oxide layers were formed weekly using a precursor, over a period of nine weeks, and the resistivity was measured. Also, the precursors were observed for signs of precipitation during the nine-week period.

Figure 9:
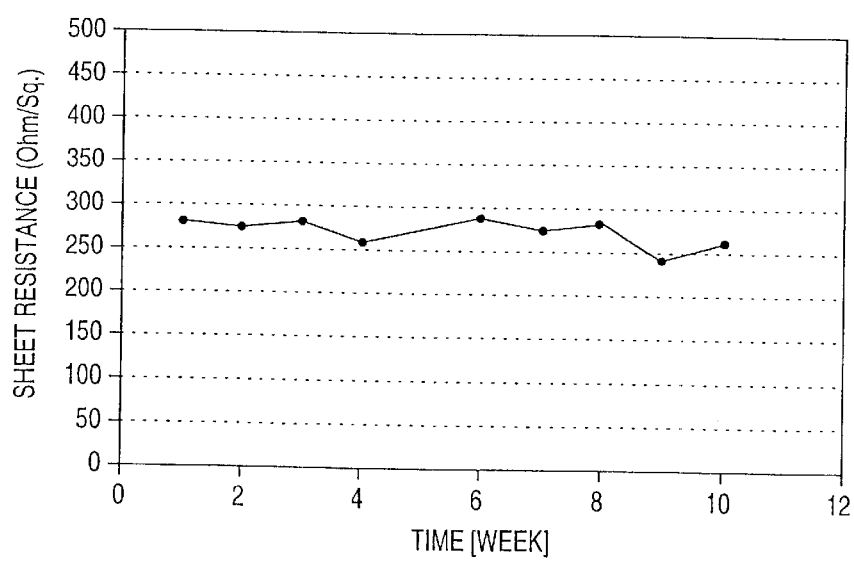
FIG. 9 is a graph of electrical resistivity in a conductive layer, fabricated using a liquid precursor after the invention, plotted as a function of storage time.

A 0.5 molar liquid precursor solution of tin 2-ethylhexanoate and antimony 2-ethylhexanoate in xylenes solvent having relative molar proportions corresponding to the stoichiometric formula $Sn_{0.97}Sb_{0.03}O_2$ was prepared in week 1. The tin-antimony liquid precursor was stored in a 20 ml bottle at room temperature. In week 1 and weekly thereafter, the tin-antimony precursor solution was deposited on silicon wafers having a 0.15 $\mu$m thermal oxide layer using a spin-on technique as in Example 3. Each wafer was soft baked at 150° C. for two minutes, and hard baked at 260° C. for four minutes. The conductive layer thin film was grown by annealing the wafer for 5 minutes at a temperature of 600° C. in forming gas with a composition of 10% $H_2$ gas in nitrogen. The thickness of the exemplary conductive layer thin films were measured to be about 60 nm. The sheet resistance of the examples was determined with a four point probe using tungsten contacts. FIG. 9 is a graph of electrical resistivity in conductive thin films, plotted as a function of storage time. The measured resistivity of the samples during the whole nine-week period varied within the range of from 245 to 290 k.Ω/square.

A 0.5 molar precursor solution of tin 2-ethylhexanoate in xylenes solvent was prepared in week 1 and placed in two 20 ml bottles. One bottle was stored at room temperature, the other bottle was stored in a refrigerator. After approximately 3½ weeks, the tin liquid precursor at room temperature began to precipitate. In contrast, the tin liquid precursor stored in the refrigerator showed no signs of precipitation during the nine-week period of observation. The observations indicate that the presence of antimony in a tin-antimony liquid precursor significantly increases the shelf life of the liquid precursor. Also, refrigeration significantly increases shelf life.

EXAMPLE 5

Figure 10:
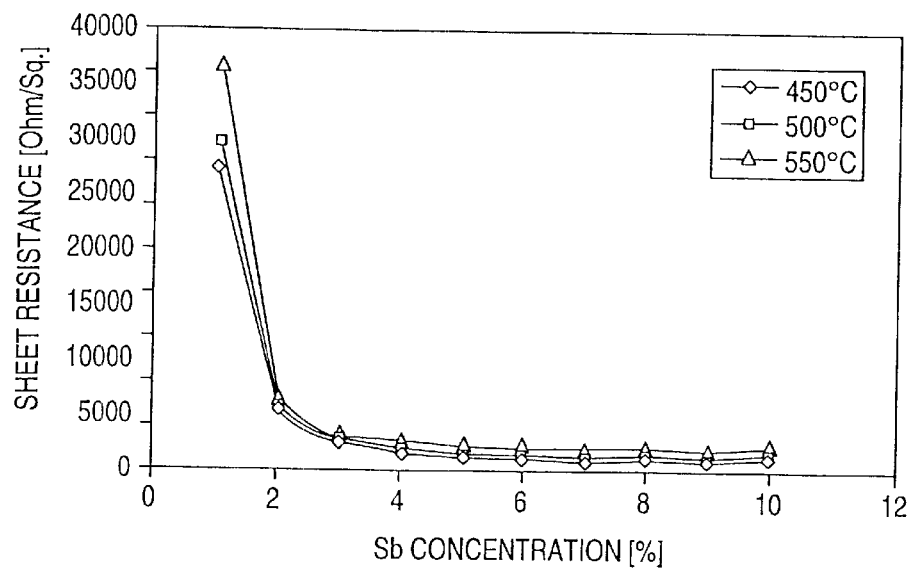
FIG. 10 is a graph of sheet resistance in a tin-antimony oxide thin film, in units of ohms/sq, plotted as a function of relative antimony concentration (mole percent)

Inventive liquid precursors in which the concentration of antimony was varied in the range of 1–10% were used to make tin-antimony thin films having a thickness in the range 60–80 nm. Thin films were deposited and baked as in Example 3, then annealed in forming gas at 450, 500 and 550° C., and the sheet resistance of each film was measured. FIG. 10 is a graph of sheet resistance, in units of ohms/sq, plotted as a function of relative antimony concentration (mole percent). The data show generally that both annealing temperature and relative concentration of a plurality of metals in an inventive precursor significantly influence the resistivity of the metal oxide thin film.

EXAMPLE 6

Figure 11:
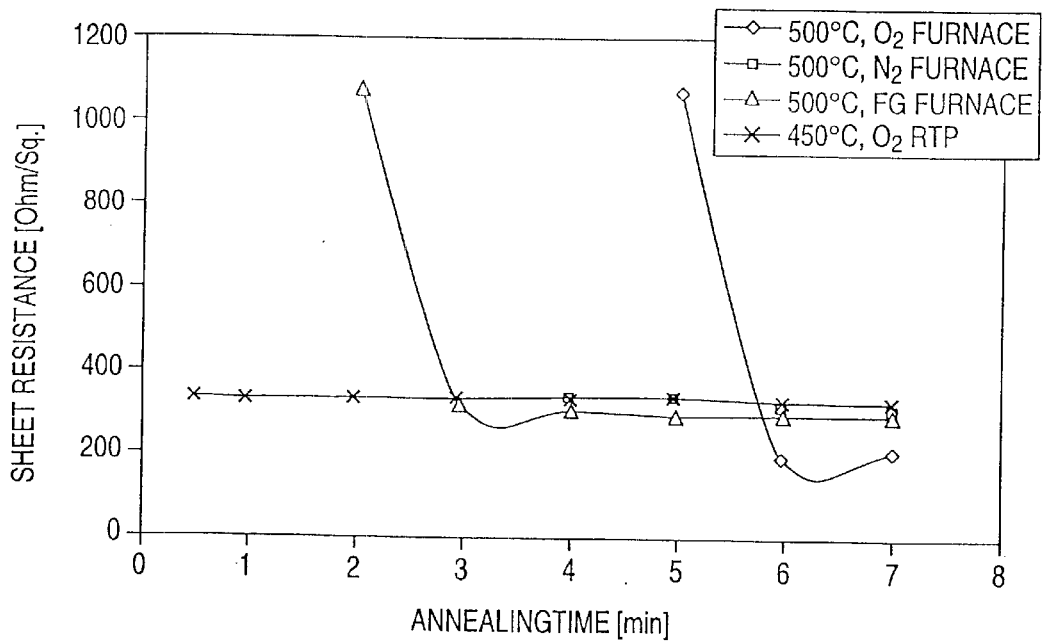
FIG. 11 is a graph of sheet resistance in tin-antimony oxide thin films, in units of ohms/sq, plotted as a function of annealing time in minutes.

Inventive liquid precursors in which the concentration of tin was 97% and the concentration of antimony was 3% were used to make tin-antimony thin films under various annealing conditions. Thin films having a thickness in the range 60–80 nm were deposited and baked as in Example 3, then annealed at 500° C. in $O_2$, $N_2$, or forming gas ("FG") ambient. Also, a set of thin films was annealed using a rapid thermal process ("RTP") with a ramp rate of 100°/sec with 450° C. hold temperature. FIG. 11 is a graph of sheet resistance, in units of ohms/sq, plotted as a function of annealing time in minutes. The data show generally that annealing time, ramping rate, and ambient atmosphere influence the resistivity of the metal oxide thin film.

EXAMPLE 7

Figure 12:
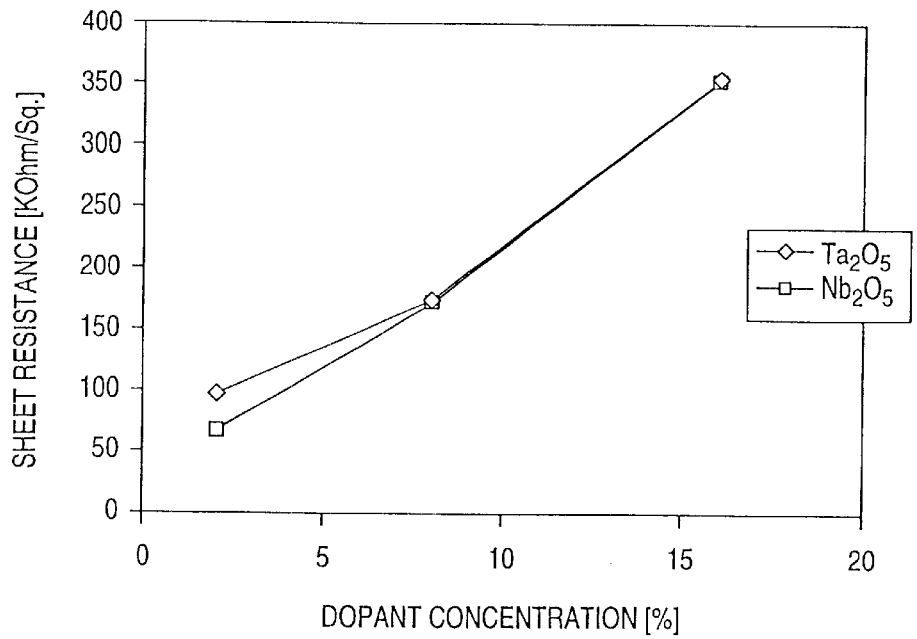
FIG. 12 is a graph of sheet resistance in tin-antimony oxide thin films, in units of Kohms/sq, plotted as a function of additional oxide ($Nb_2O_5$ and $Ta_2O_5$) concentration (mole percent)

Inventive liquid precursors having relative molar proportions of tin and antimony corresponding to the stoichiometric formula $Sn_{0.97}Sb_{0.03}O_2$ were modified by adding a tantalum or niobium precursor compound and used to make tin-antimony oxide thin films having a thickness of 120 nm and containing $Nb_2O_5$ or $Ta_2O_5$. Thin films were deposited and baked as in Example 3, then annealed in forming gas at 475° C., and the sheet resistance of each film was measured. FIG. 12 is a graph of sheet resistance, in units of Kohms/sq, plotted as a function of additional oxide ($Nb_2O_5$ or $Ta_2O_5$) concentration (mole percent). The data show generally that relative concentration of a plurality of metals in an inventive precursor significantly influences the resistivity of the metal oxide thin film. Since $Nb_2O_5$ and $Ta_2O_5$ are relatively nonconductive, an increase in their concentration increases resistivity of the thin film.

EXAMPLE 8

Figure 13:
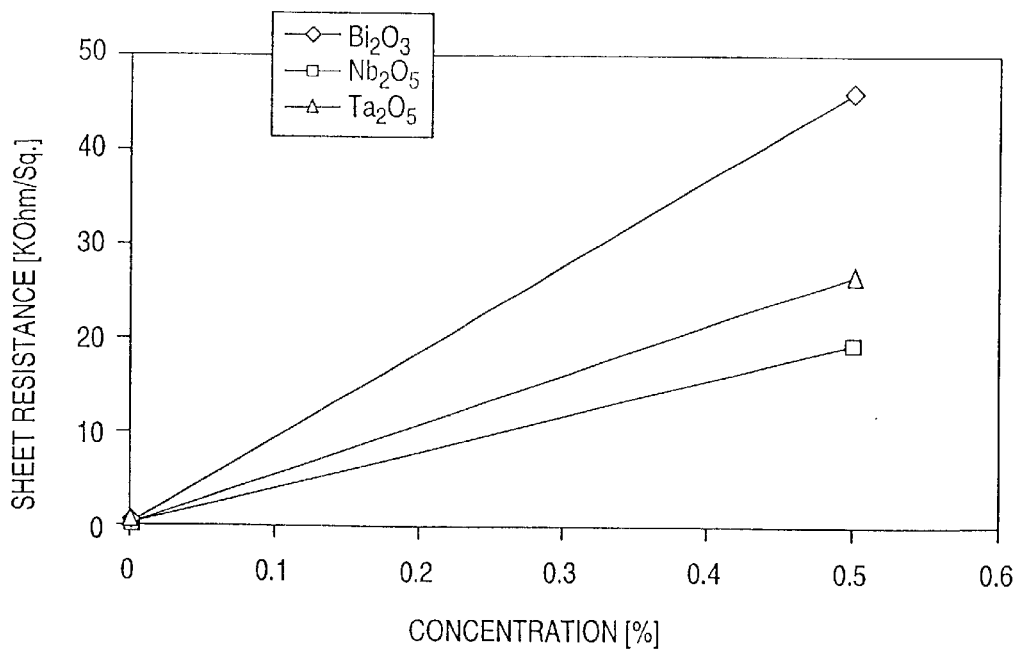
FIG. 13 is a graph of sheet resistance in tin-antimony oxide thin films, in units of Kohms/sq, plotted as a function of additional oxide concentration (mole percent of $Bi_2O_3$, $Nb_2O_5$ and $Ta_2O_5$)

Inventive liquid precursors having relative molar proportions of tin and antimony corresponding to the stoichiometric formula $Sn_{0.97}Sb_{0.03}O_2$ were modified by adding 0.5% relative amount of a bismuth, niobium or tantalum precursor compound. The precursors were used to make tin-antimony oxide thin films having a thickness of 120 nm and containing $Nb_2O_5$ or $Ta_2O_5$. Thin films were deposited and baked as in Example 3, then annealed in forming gas at 475° C., and the sheet resistance of each film was measured. FIG. 13 is a graph of sheet resistance, in units of Kohms/sq, plotted as a function of additional oxide concentration ((mole percent of $Bi_2O_3$, $Nb_2O_5$ or $Ta_2O_5$). The data show generally that a dopant amount of a precursor compound for a nonconductive oxide significantly influences the resistivity of the metal oxide thin film. The resistivity of a $Sn_{0.97}Sb_{0.03}O_2$ thin film without dopant was about 0.3 Kohm/sq. The addition of 0.5% of dopant precursor compound increased the resistivity value to the range of 20–47 Kohm/sq.

EXAMPLE 9

Figure 14:
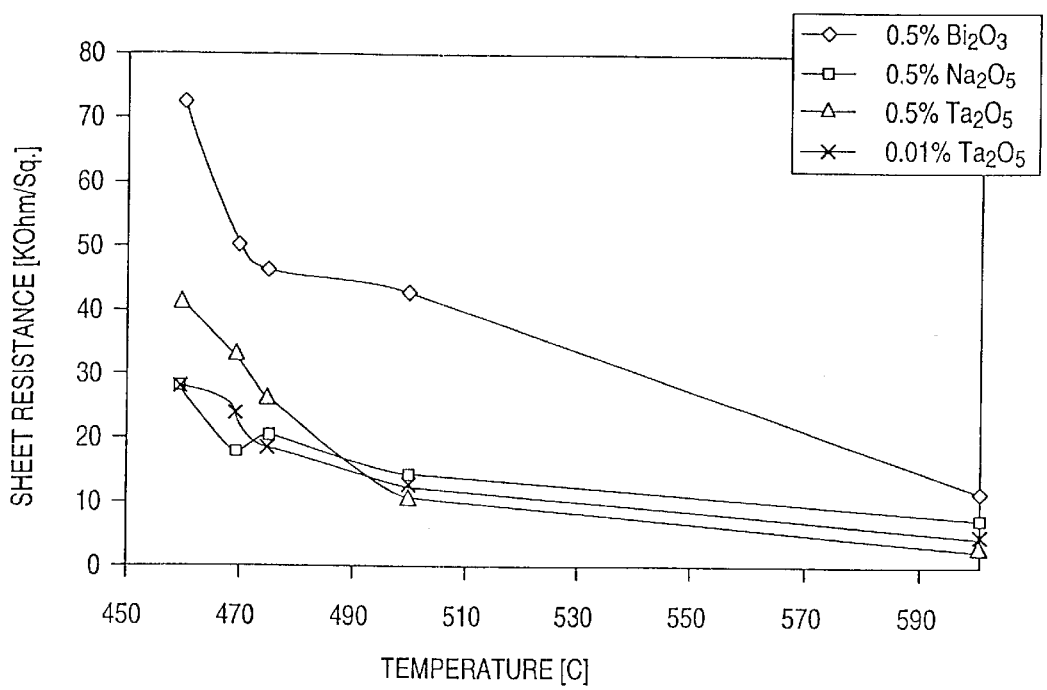
FIG. 14 is a graph of sheet resistance in doped tin-antimony oxide thin films, in units of Kohms/sq, plotted as a function of annealing temperature.

Inventive liquid precursors having relative molar proportions of tin and antimony corresponding to the stoichiometric formula $Sn_{0.97}Sb_{0.03}O_2$ were modified by adding a bismuth, niobium or tantalum precursor compound, corresponding to one of 0.5% $Bi_2O_3$, 0.5% $Nb_2O_5$, 0.5% $Ta_2O_5$ or 0.01% $Ta_2O_5$. The precursors were used to make thin films, which were deposited and baked as in Example 3, then annealed in forming gas for 5 minutes at one of 460, 470, 475, 500 or 600° C. FIG. 14 is a graph of sheet resistance, in units of Kohms/sq, plotted as a function of annealing temperature. The data show generally that selection of dopant and annealing temperature of a thin film deposited using an inventive precursor significantly influences the resistivity of the metal oxide thin film. In films annealed at a lower annealing temperature of 460° C., the measured resistivity was in the range of 27 to 72 Kohm/sq. Also, the composition of dopant was more significant at lower annealing temperatures. As annealing temperature increased, the composition of the tested dopants became less significant, and the resistivity in all films decreased to a value in the range 5–10 Kohm/sq after annealing at 600° C.

EXAMPLE 10

Figure 15:
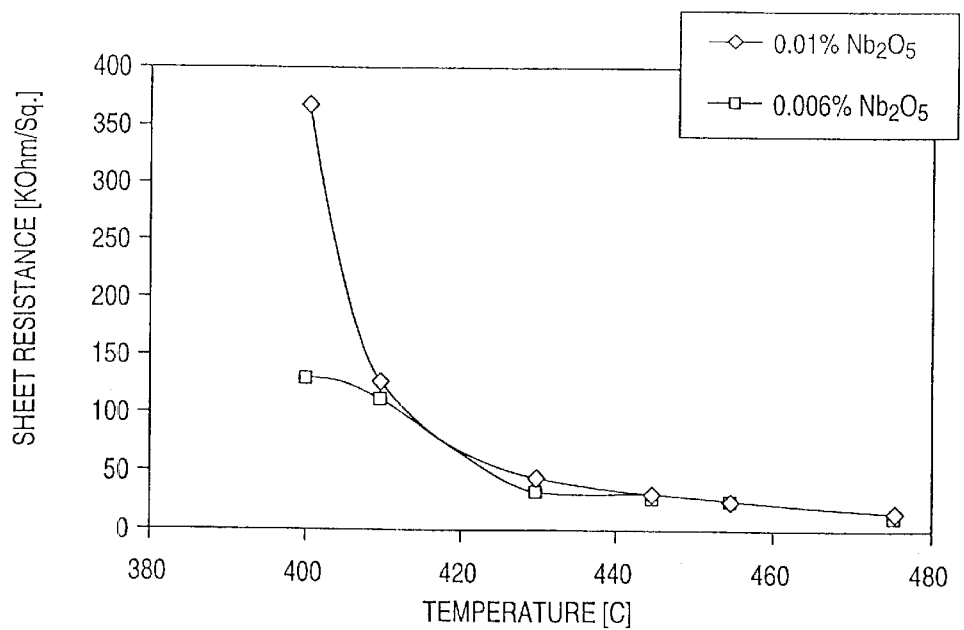
FIG. 15 is a graph of sheet resistance in doped tin-antimony oxide thin films, in units of Kohms/sq, plotted as a function of annealing temperature.

Inventive liquid precursors having relative molar proportions of tin and antimony corresponding to the stoichiometric formula $Sn_{0.97}Sb_{0.03}O_2$ were modified by adding a niobium precursor compound, corresponding to one of 0.006 or 0.01 % $Nb_2O_5$. The precursors were used to make thin films, which were deposited and baked as in Example 3, then annealed in forming gas for 5 minutes at one of 460, 470, 475, 500 or 600° C. FIG. 15 is a graph of sheet resistance, in units of Kohms/sq, plotted as a function of annealing temperature. The data show generally that selection of dopant concentration at a low annealing temperature significantly influences the resistivity of the metal oxide thin film. After annealing at 400° C., the thin film made using the 0.01% $Nb_2O_5$ precursor had a resistivity of 367 Kohm/sq. In contrast, the resistivity in the thin film made from the 0.0006% $Nb_2O_5$ precursor had a resistivity of 132 Kohm/sq.

FIG. 15 shows that the effect of dopant concentration decreases as anneal temperature increases, and that resistivity may sharply decrease as anneal temperature increases above 400° C. In films annealed at a higher annealing temperature of 475° C., the measured resistivity was about 10 Kohm/sq.

Examples 5–10 show how resistivity, in particular, and electrical properties, in general, of metal oxide thin films made with inventive precursors can be advantageously controlled by selecting the composition of an inventive precursor in view of fabrication operating parameters, such as annealing temperature, ambient anneal atmosphere, and annealing time, among others.

There has been described novel liquid precursors for fabricating transparent metal oxide thin film layers in fluorescent lamps, flat panel displays and other electrooptical devices. The novel precursors are used in metal organic decomposition techniques, in which a metal organic liquid precursor solution containing one or more metal organic liquid precursor compounds is applied to a substrate surface, where heat causes reaction and the formation of the desired metal oxide thin film layer. Selective combination of thin film layer composition and annealing temperature allows control of electrical resistivity. The invention, therefore, includes new compositions of, and methods of preparing, metal organic liquid precursor solutions. The liquid precursors of the invention are useful for forming transparent metal oxide thin films that inhibit the generation of "measles", or "black spot defects", in fluorescent lamps, thereby improving their appearance and operating performance. The invention also provides greater efficiency and control in the manufacture of transparent metal oxide thin film layers in electrooptical devices. It should be understood that the particular embodiments shown in the drawings and described within this specification are for purposes of example and should not be construed to limit the invention, which will be described in the claims below. For example, the invention contemplates that the metal organic liquid precursor solutions of the invention may comprise a wide range of different types of metal organic precursor compounds that can be deposited and decomposed using metal organic decomposition techniques. Similarly, transparent metal oxide thin films of electrooptical devices may comprise materials of various compositions and thicknesses. By selective treatment, thin films formed using the liquid precursors of the invention may have different electrical properties, even if they have the same chemical composition. It is evident that those skilled in the art may now make numerous uses and modifications of the specific embodiments described, without departing from the inventive concepts. It is also evident that the steps recited may in some instances be performed in a different order; or equivalent structures and processes may be substituted for the structures and processes described. Consequently, the invention is to be construed as embracing each and every novel feature and novel combination of features present in and/or possessed by the liquid precursor compositions and liquid precursor preparation methods described.

What is claimed is:

1. A nonaqueous metal organic liquid precursor solution comprising an organic precursor compound, said solution containing a first metal and a second metal different from said first metal, wherein said first metal is selected from the group consisting of tin, antimony, and indium, and said second metal is selected from the group consisting of tin, antimony, and indium.

2. A nonaqueous metal organic liquid precursor solution as in claim 1 wherein said first is tin.

3. A nonaqueous metal organic liquid precursor solution as in claim 1 wherein said first metal is antimony.

4. A nonaqueous metal organic liquid precursor solution as in claim 1 wherein said first metal is indium.

5. A nonaqueous metal organic liquid precursor solution as in claim 1, further comprising an organic dopant precursor compound containing a metal selected from the group consisting of niobium, tantalum, bismuth, cerium, yttrium, titanium, zirconium, hafnium, silicon, zinc and magnesium.

6. A nonaqueous metal organic liquid precursor solution as in claim 1 wherein said first metal comprises tin and said second metal comprises antimony.

7. A nonaqueous metal organic liquid precursor solution as in claim 1 wherein said first metal comprises tin and said second metal comprises indium.

8. A nonaqueous metal organic liquid precursor solution as in claim 1 wherein said metal organic liquid precursor solution contains metal moieties in effective amounts for forming an oxide selected from the group consisting of $SnO_2$, $Sb_2O_3$, and $In_2O_3$.

9. A nonaqueous metal organic liquid precursor solution as in claim 1 wherein said organic precursor compound is selected from the group consisting of alkoxycarboxylates, carboxylates and alkoxides.

10. A nonaqueous metal organic liquid precursor solution as in claim 1 wherein said organic precursor compound is selected from the group consisting of ethylhexanoates, octanoates, and neodecanoates.

11. A nonaqueous metal organic liquid precursor solution as in claim 10 wherein said organic precursor compound comprises a metal ethylhexanoate.

12. A nonaqueous metal organic liquid precursor solution as in claim 11 wherein said organic precursor compound comprises tin 2-ethylhexanoate.

13. A nonaqueous metal organic liquid precursor solution as in claim 11 wherein said organic precursor compound comprises antimony 2-ethylhexanoate.

14. A nonaqueous metal organic liquid precursor solution as in claim 11 wherein said organic precursor compound comprises indium 2-ethylhexanoate.

15. A nonaqueous metal organic liquid precursor solution comprising an organic precursor compound containing a first metal selected from the group consisting of tin, antimony, and indium and an organic dopant precursor compound containing a metal selected from the group consisting of niobium, tantalum, bismuth, cerium, yttrium, titanium, zirconium, hafnium, silicon, zinc and magnesium.

16. A nonaqueous metal organic liquid precursor solution as in claim 15 wherein said organic dopant precursor compound is selected from the group consisting of alkoxycarboxylates, carboxylates and alkoxides.

17. A nonaqueous metal organic liquid precursor solution as in claim 15 wherein said organic dopant precursor compound is selected from the group consisting of ethylhexanoates, octanoates, and neodecanoates.

18. A nonaqueous metal organic liquid precursor solution as in claim 15 wherein said organic dopant precursor compound contains a metal selected from the group consisting of niobium, tantalum, and bismuth.

19. A nonaqueous metal organic liquid precursor solution as in claim 18 wherein said precursor solution contains metal moieties in effective amounts for forming metal oxide material having a stoichiometric formula $Sn_{1-x}Sb_xO_2$, where $0.001 \leq x \leq 0.3$, combined with dopant selected from the group consisting of $Nb_2O_5$, $Ta_2O_5$ and $Bi_2O_3$, with a relative molar concentration in the range of from 0.001 to 1.0 mole percent.

20. A nonaqueous metal organic liquid precursor solution as in claim 19 wherein said liquid precursor solution contains metal moieties in effective amounts for forming said metal oxide having a stoichiometric formula $Sn_{0.97}Sb_{0.03}O_2$ with 0.006 mole percent $Nb_2O_5$ dopant.

21. A nonaqueous metal organic liquid precursor solution as in claim 1 wherein said metal organic liquid precursor solution further comprises a solvent, and said solvent is selected from the group consisting of alcohols, aromatic hydrocarbons, and esters.

22. A nonaqueous metal organic liquid precursor solution as in claim 1 wherein said metal organic liquid precursor solution further comprises a solvent, and said solvent is selected from the group consisting of xylenes, n-octane, 2-methoxyethanol, n-butyl acetate, 1,4-dioxane, methanol and methyl ethyl ketone.

23. A nonaqueous metal organic liquid precursor solution as in claim 15 wherein said organic precursor compound is selected from the group consisting of alkoxycarboxylates, carboxylates and alkoxides.

24. A nonaqueous metal organic liquid precursor solution as in claim 15 wherein said organic precursor compound is selected from the group consisting of ethylhexanoates, octanoates, and neodecanoates.

25. A nonaqueous metal organic liquid precursor solution as in claim 15 wherein said organic precursor compound comprises a metal ethylhexanoate.

26. A nonaqueous metal organic liquid precursor solution as in claim 15 wherein said metal organic liquid precursor solution further comprises a solvent, and said solvent is selected from the group consisting of alcohols, aromatic hydrocarbons, and esters.

27. A nonaqueous metal organic liquid precursor solution as in claim 15 wherein said solvent is selected from the group consisting of xylenes, n-octane 2-methoxyethanol, n-butyl acetate, 1,4-dioxane, methanol and methyl ethyl ketone.

* * * * *